(12) United States Patent
Wingfield et al.

(10) Patent No.: US 10,215,710 B2
(45) Date of Patent: Feb. 26, 2019

(54) METHOD FOR CLASSIFYING A DEFECT IN A COMPONENT INTENDED TO HAVE A MONOCRYSTALLINE STRUCTURE

(71) Applicant: ROLLS-ROYCE plc, London (GB)

(72) Inventors: Michael J. Wingfield, Derby (GB); Adriano Pulisciano, Birmingham (GB)

(73) Assignee: ROLLS-ROYCE plc, London (GB)

( * ) Notice: Subject to any disclaimer, the term of this patent is extended or adjusted under 35 U.S.C. 154(b) by 135 days.

(21) Appl. No.: 15/267,833

(22) Filed: Sep. 16, 2016

(65) Prior Publication Data
US 2017/0108449 A1  Apr. 20, 2017

(30) Foreign Application Priority Data

Oct. 16, 2015  (GB) .................................. 1518322.1

(51) Int. Cl.
*G01N 21/95* (2006.01)
*G01N 21/55* (2014.01)
(Continued)

(52) U.S. Cl.
CPC ......... *G01N 21/95* (2013.01); *G01N 21/4788* (2013.01); *G01N 21/55* (2013.01);
(Continued)

(58) Field of Classification Search
CPC .... G01N 21/95; G01N 21/55; G01N 2201/12; G01N 2201/062
(Continued)

(56) References Cited

U.S. PATENT DOCUMENTS 5,774,212 A  6/1998  Corby, Jr.
6,603,542 B1  8/2003  Chase et al.
(Continued)

FOREIGN PATENT DOCUMENTS

EP  1494275 A1  1/2005
EP  2 846 155 A1  3/2015
(Continued)

OTHER PUBLICATIONS

Mar. 17, 2017 European Search Report issued in European Patent Application No. 16 18 9184.
(Continued)

*Primary Examiner* — Hina F Ayub
*Assistant Examiner* — Amanda Merlino
(74) *Attorney, Agent, or Firm* — Oliff PLC

(57) ABSTRACT

Method and apparatus for classifying defect in component having a monocrystalline structure. The method includes: illuminating surface of component containing defect with beam of light from plurality of different spherical directions; each illumination direction, measuring intensity of light reflected by surface and received by detector; determining contrast value between region with higher intensity and a region with lower intensity for each illumination direction; analyzing contrast values by performing tests selected from the following: (a) determining whether region with higher intensity exceeds predetermined width; (b) identifying illumination direction which produces maximum contrast value, and determining whether illumination direction falls outside of predetermined region; (c) identifying peak in contrast values and determining whether peak extends over range of illumination directions which exceeds predetermined threshold; and (d) determining whether contrast values contain plurality of discontinuous peaks; and determining type of defect based on of tests.

17 Claims, 22 Drawing Sheets

(51) Int. Cl.
    *G01N 21/47* (2006.01)
    *G01N 21/88* (2006.01)
    *G01N 21/84* (2006.01)

(52) U.S. Cl.
    CPC ..... *G01N 21/8806* (2013.01); *G01N 21/8422* (2013.01); *G01N 21/9515* (2013.01); *G01N 2021/8477* (2013.01); *G01N 2201/062* (2013.01); *G01N 2201/12* (2013.01)

(58) Field of Classification Search
    USPC .......................................... 356/237.1–237.6
    See application file for complete search history.

(56) References Cited

U.S. PATENT DOCUMENTS

| | | | |
|---|---|---|---|
| 6,724,474 B1 | 4/2004 | Heo et al. | |
| 6,788,411 B1 | 9/2004 | Lebens | |
| 7,034,931 B2 * | 4/2006 | Jones | G01N 21/4788 |
| | | | 356/237.2 |
| 2001/0030296 A1 | 10/2001 | Ishimaru et al. | |
| 2011/0180727 A1 | 7/2011 | Kell et al. | |

FOREIGN PATENT DOCUMENTS

| | | |
|---|---|---|
| EP | 2 846 156 A1 | 3/2015 |
| GB | 1 431 902 A | 4/1976 |

OTHER PUBLICATIONS

Apr. 6, 2016 Search Report issued in British Patent Application No. GB 1518322.1.

\* cited by examiner

METHOD FOR CLASSIFYING A DEFECT IN A COMPONENT INTENDED TO HAVE A MONOCRYSTALLINE STRUCTURE

The disclosure relates to a method for classifying a defect in a component intended to have a monocrystalline structure and particularly, but not exclusively to a method which is able to automatically distinguish between defects found in turbine blades.

Metals may be cast such that they exhibit a single crystal (monocrystalline) structure in which the crystal lattice of the entire sample is continuous, with no grain boundaries. Such a crystal structure decreases the amount of creep exhibited by the metal. Accordingly, monocrystalline metals are particularly advantageous for components which are exposed to high temperatures, such as turbine blades.

As shown in FIG. 1, secondary grain(s) have a different crystal orientation to the primary grain (the rest of the turbine blade). X-ray crystallography may be used to examine the crystal structure and identify the presence of unwanted secondary grains in the crystal structure of turbine blades. However, such techniques are costly and time consuming.

Turbine blades are typically manufactured such that the primary grain orientation is substantially aligned with the major (longitudinal) axis of the turbine blade. Secondary grains (when they form) have a tendency to deviate from the primary grain in quite a predictable way having a dominant component angle which is often close to the long axis of the blade and the primary grain structure. As a result, secondary grain defects can often be seen when rotating the blade around its longitudinal axis under a white light source. Visual/optical inspection techniques can therefore be used to identify secondary grains (possibly, with subsequent confirmation using X-ray crystallography). However, existing visual inspection techniques cannot easily distinguish between different types of defect and require significant operator input.

It is therefore desired to provide a more repeatable and informative technique.

In accordance with an aspect of the disclosure, there is provided a method for classifying a defect in a component intended to have a monocrystalline structure, the method comprising: illuminating a surface of a component containing a defect with a beam of light from a plurality of different spherical directions centred on the surface; for each illumination direction, measuring the intensity of light reflected by the surface and received by a detector; determining a contrast value between a region with higher intensity and a region with lower intensity for each illumination direction; analysing the contrast values by performing a plurality of tests selected from the following: (a) determining whether the region with higher intensity exceeds a predetermined width; (b) identifying an illumination direction which produces a maximum contrast value, and determining whether this illumination direction falls outside of a predetermined region centred on the detector; (c) identifying a peak in the contrast values and determining whether the peak extends over a range of illumination directions which exceeds a predetermined threshold; and (d) determining whether the contrast values contain a plurality of discontinuous peaks; and determining the type of defect based on the outcome of the plurality of tests.

The type of defect may be determined to be either a scratch or a secondary grain.

The result of each of the plurality of tests may be allocated a score and the total score is used to determine whether the defect is a scratch or a secondary grain.

The defect may be determined as a secondary grain if more than half of the tests are positive.

The defect may be determined as a scratch if less than half of the tests are positive.

The method may further comprise, if the defect is determined as a secondary grain, determining the number of peaks defined by the contrast values; and, if there are four peaks, identifying the defect as an ultra-high angle grain defect.

The method may further comprise, if the defect is determined as a scratch, determining the severity of the scratch based on the height of the peak in the contrast values.

Analysing the contrast values may be performed automatically by a computer-implemented analysis algorithm.

The surface may be illuminated by a plurality of light sources arranged in an arc and the component is rotated relative to the light sources by set increments to define the spherical directions.

The illumination direction may be defined by a lighting angle of the light source on the arc and a B axis angle of the component.

Test (c) may determine whether the peak extends over a range of lighting angles which exceeds a predetermined threshold. Test (d) may determine whether the peaks are discontinuous across the B axis angles.

The contrast value may be determined by measuring the intensity of light along a line intersecting the defect.

The contrast value may be determined by measuring the intensity of each pixel within a box containing the defect and plotting the intensity of the pixels on a histogram.

The contrast value may be determined by measuring the intensity of light reflected by the defect and the intensity of light reflected by a non-defected region.

The intensity of light reflected by the defect may be measured for each pixel of a box located entirely within the defect and the intensity of light reflected by the non-defected region may be measured for each pixel of a box located entirely within the non-defected region.

The intensity of the pixels may be plotted on a histogram for the defect and a histogram for the non-defected region. The histograms of the defect and non-defected regions may be a single plot.

The component may be a turbine blade.

In accordance with an aspect of the disclosure, there is provided an apparatus for classifying a defect in a component intended to have a monocrystalline structure, the apparatus comprising: a lighting rig having a light source for illuminating a surface of a component containing a defect and a detector for measuring the intensity of light reflected by the surface; and a computer system configured to execute some or all of the steps of any of the preceding claims.

For a better understanding of the disclosure, and to show more clearly how it may be carried into effect, reference will now be made, by way of example, to the accompanying drawings, in which:—

Figure 19A:
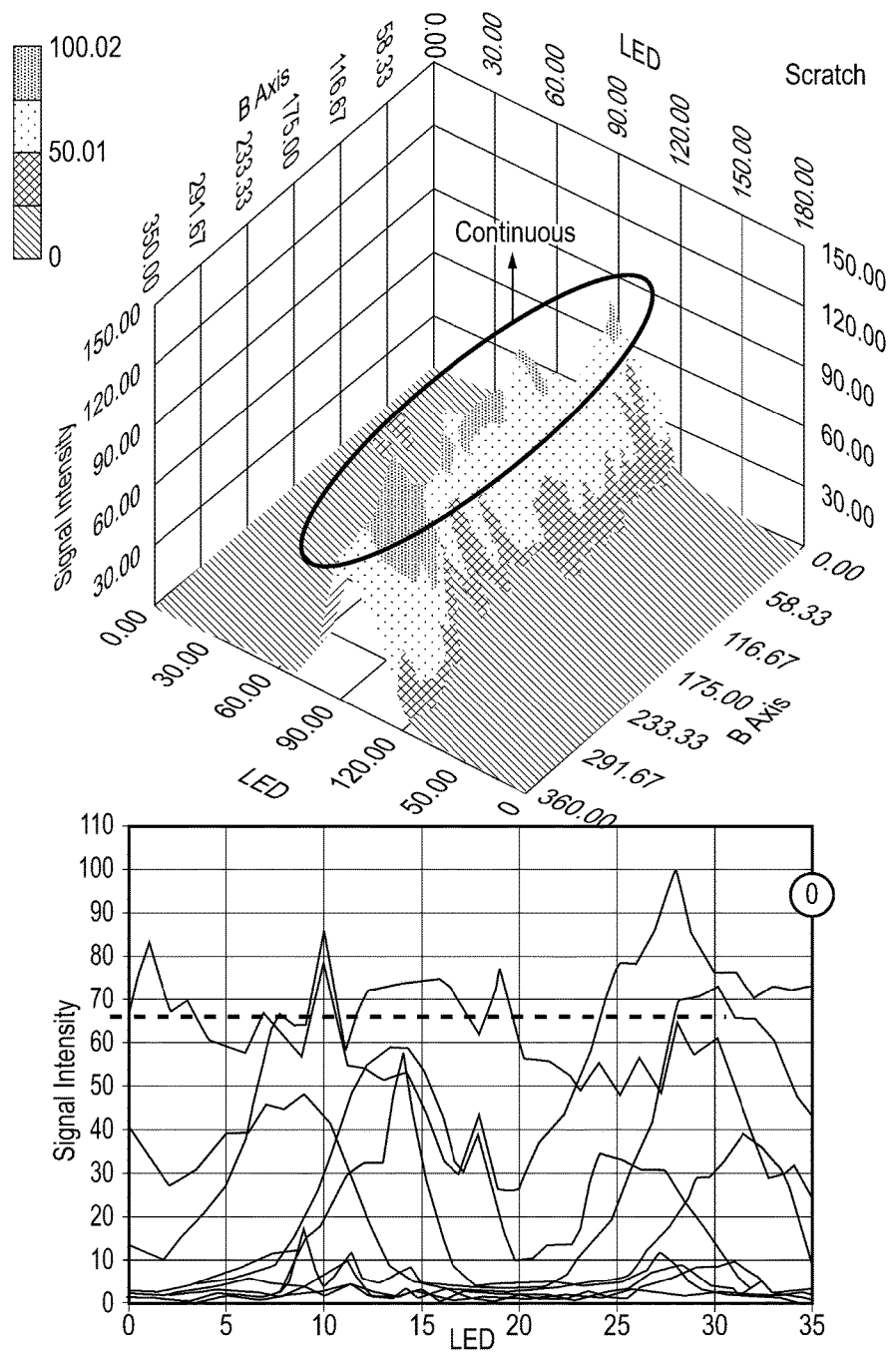

FIG. 19A an illustration of a fourth test for distinguishing between secondary grain defects and scratches, and receiving a score of "0."

Figure 19B:
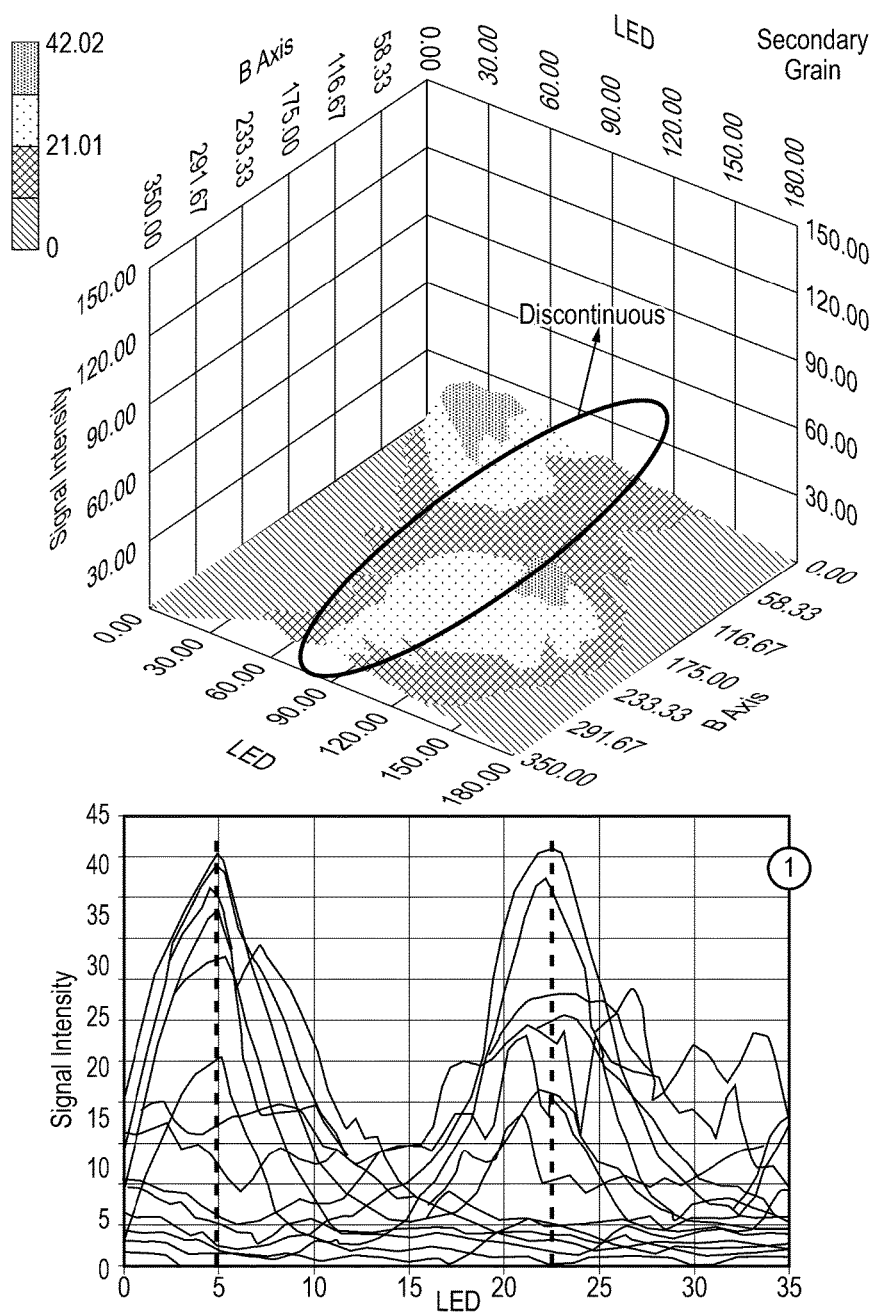

FIG. 19B is an illustration of a fourth test for distinguishing between secondary grain defects and scratches, and receiving a score of "1."

Figure 20:
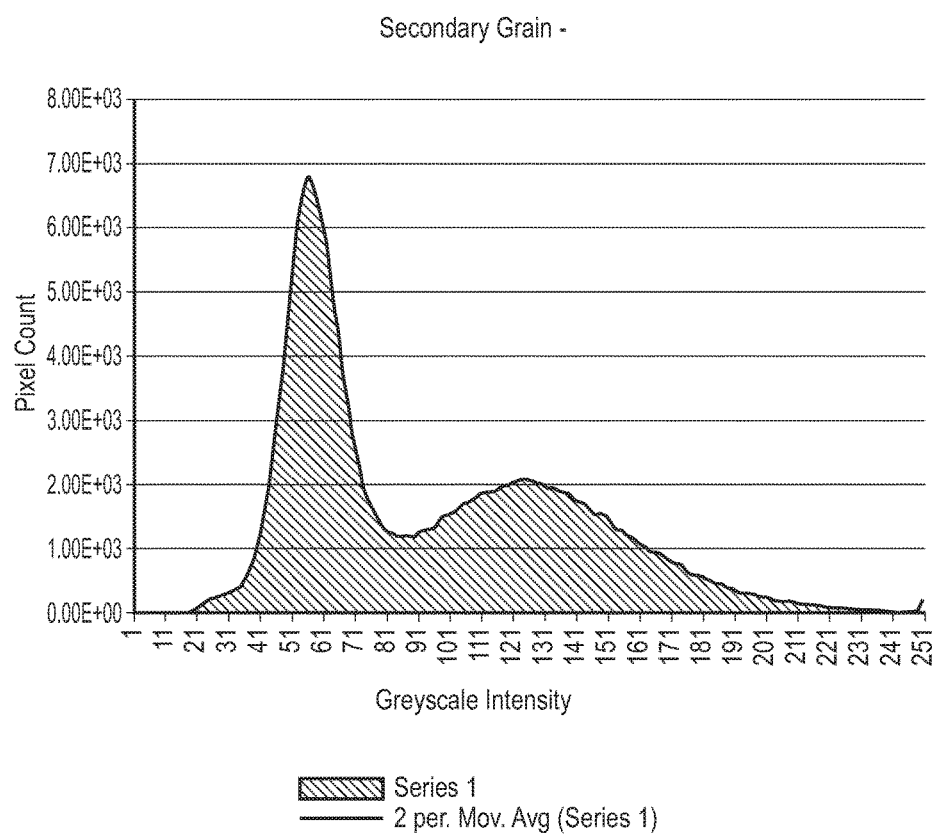

FIG. 20 is a histogram showing greyscale intensity as a function of pixel count.

Figure 2:
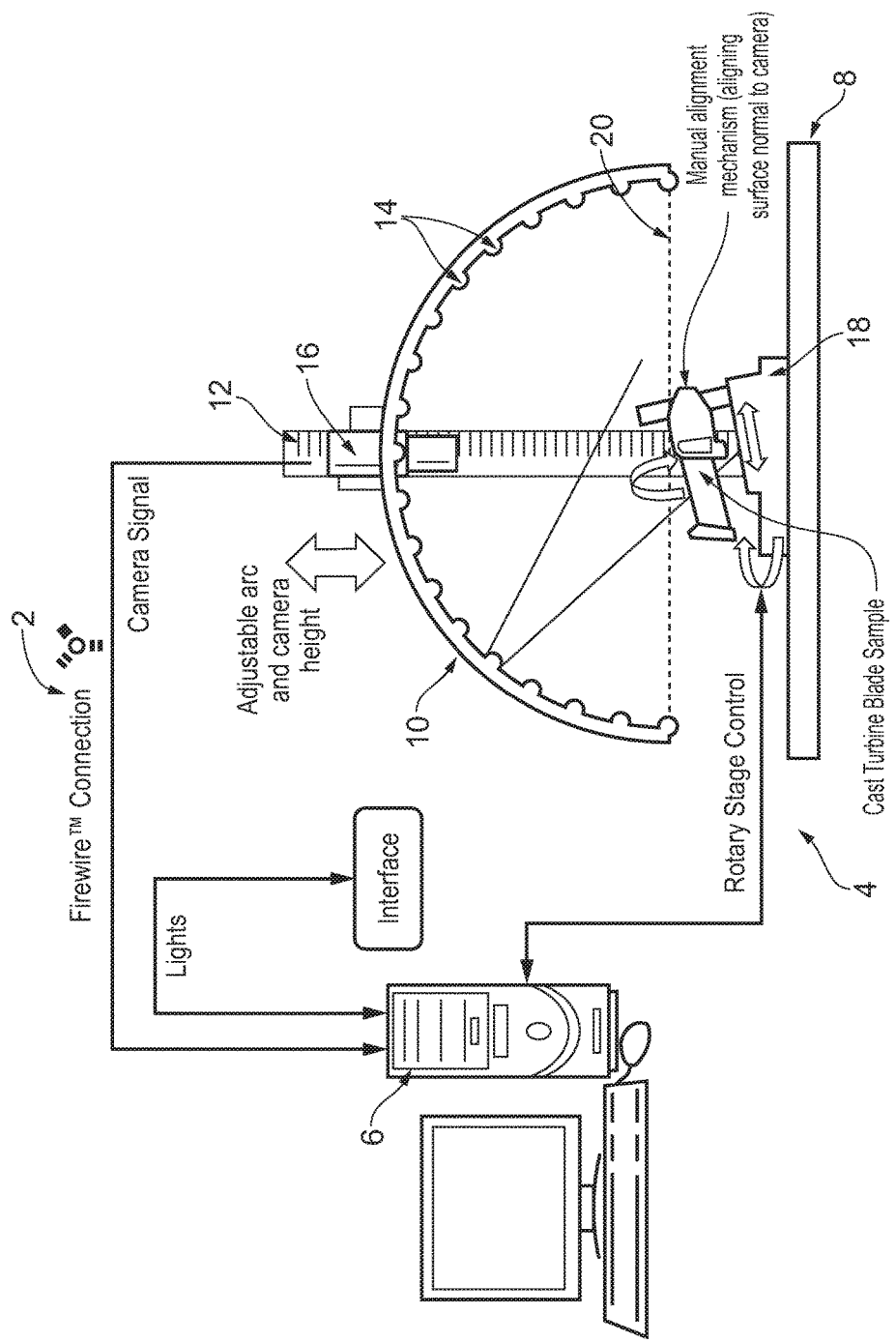
FIG. 2 is a schematic view of a testing system.

FIG. 2 shows a testing system 2 which generally comprises an imaging rig 4 and a computer system 6.

The imaging rig 4 comprises a base plate 8. A lighting arc 10 is suspended above the base plate 10 by a pillar 12 which extends from the base plate 8. The pillar 12 allows the position of the lighting arc 10 above the base plate 8 to be adjusted, as will be described further below.

The lighting arc 10 has a semicircular profile. A plurality of lighting strips 14 extend widthwise across the lighting arc 10 in rows. Each lighting strip 14 comprises a plurality of bright white LEDs. The LEDs can be easily switched on and off with minimal warm up and cool down times and have a well-defined lighting cone angle (of) 55°. The lighting strips 14 are located at different angles around the semicircular arc 10. In the example shown, the lighting arc 10 has eighteen lighting strips 14 which are provided at 10° increments from 0° to 180°, but excluding 90° (the zenith of the lighting arc 10). The LEDs of each lighting strip 14 are parallel to one another and directed towards the centre of the semicircle. As a result, the LEDs of the lighting strips 14 located at the 0° and 180° positions face one another. The light patch generated by each row of LEDs is coincident at the same line in the centre of the arc.

A high-resolution digital camera 16 is located at the zenith of the lighting arc 10 (i.e. at the 90° position). The camera protrudes through a hole in the lighting arc 10 and is directed towards the centre of the semicircle (i.e. vertically downwards).

A motorised rotary stage 18 is located at the centre of the base plate 8 such that the centre of the rotary stage 18 is aligned with the camera 16. The rotary stage 18 comprises a blade mount which holds a turbine blade for inspection. The blade mount is connected to the rotary stage 18 by a ball and socket joint to allow maximum alignment flexibility.

The computer system 6 is connected to the lighting strips 14, the camera 16 and the rotary stage 18. The computer system 6 executes software which controls the imaging rig 4 and analyses images captured by the camera 16, as will be described in detail below.

In order to inspect a defect located in a turbine blade, the blade is mounted in the blade mount of the rotary stage 18 and aligned so that the surface normal of the defect points towards the camera 16 and is centralised to the imaging rig 4. The lighting arc 10 may be translated along the pillar 12 toward or away from the base plate 8 so that the surface under inspection is level with the base line of the arc 20.

With the turbine blade correctly position, the computer system 6 executes a test routine using the imaging rig 4. In the test route, each lighting strip 14 is illuminated in turn and a monochromatic still image is captured each time by the camera 16. This procedure is repeated at multiple rotary stage (B axis) positions until an entire hemisphere of images has been obtained. For example, the rotary stage may be rotated by 10° increments, such that 648 images are generated (18 lighting strips and 36 B axis positions). This process is automated by the computer system 6.

The image sample area of the blade may be defined using labels or other markings. For example, a user may attach two labels to the surface of the blade across a grain boundary. Pattern matching techniques are then used to ensure that the sample area is consistent throughout the test. The pattern matching technique uses the two stickers to orientate each image. As the rotary stage 18 rotates the sample window keeps track of the defect and ensures that the boundary is sampled in the same way each time.

Alternatively, a model matching technique may be used to define the sample area without the use of target stickers.

This technique allows a hemisphere of images to be obtained without the need for a physically moving light source. Further, changing the incident light source angle rather than changing the roll angle of the blade allows a wider range of incident lighting angles to be tested whilst keeping the blade within the camera's field of view. The lighting arc 10 also allows the part to be easily accessed and carefully positioned on the imaging rig 4.

The light from the illuminated lighting strip 14 reflects off the surface of the turbine blade. The different orientations of the primary and secondary grains create variations in the image captured by the camera.

Figure 1:
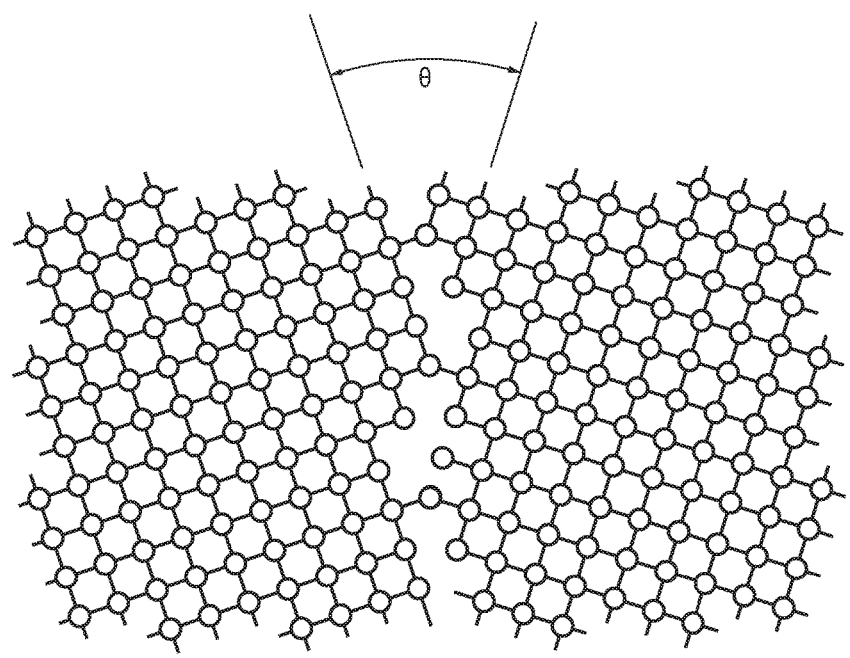
FIG. 1 is an illustration of a crystal dislocation in one plane (represented at the molecular level)

The surface of an etched blade appears as a series of blocks when viewed under a scanning electron microscope. The etching process transforms the surface by removing a thin layer of randomly orientated material known as "gamma" (which accumulates on the surface during the casting process) leaving behind what is known as the gamma prime precipitate. Gamma prime appears as a series of blocks were of (approximately 300 nm to 700 nm) arranged in terraces. For a single crystal, these blocks all have a uniform orientation which corresponds to the underlying molecular structure. However, secondary grain defects (as depicted in FIG. 1) cause the collective orientation of the blocks to change with the underlying angular offset in the crystal structure.

The terraces are thought to act like an array of tiny, well aligned retro-reflectors. Retro-reflectors return light in the same direction as they receive it. When a secondary grain defect is present, the surface contains two adjacent regions of retro-reflectors. The collective orientation of the retro-reflectors in one region differs from the other region, the severity of which is quantified by the boundary angle.

Figure 3:
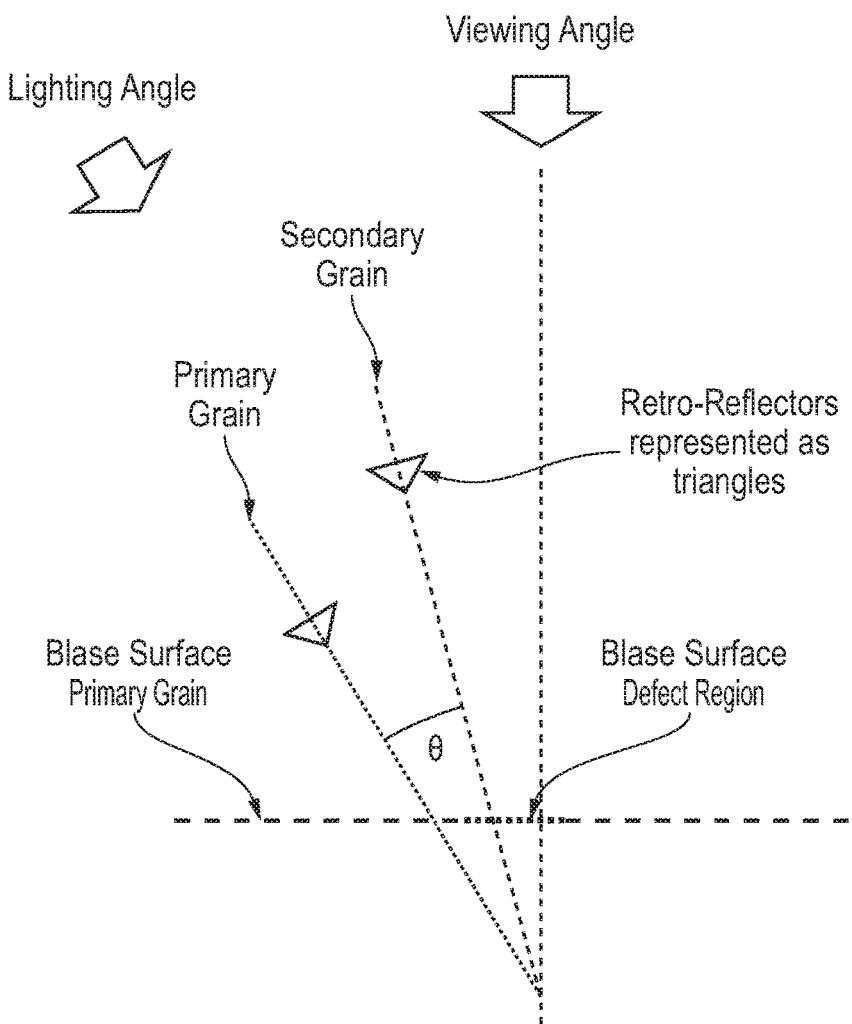
FIG. 3 is a conceptual representation of the reflection of light from a surface having primary and secondary grains.

FIG. 3 shows a diagram of this concept. The reflection planes of the primary and secondary grains are depicted as retro-reflectors centred on lines projected from the centre of the blade.

Once the images have been captured from the camera 16 by the computer system 6, they may be analysed to extract more information regarding the defect.

Figure 4:
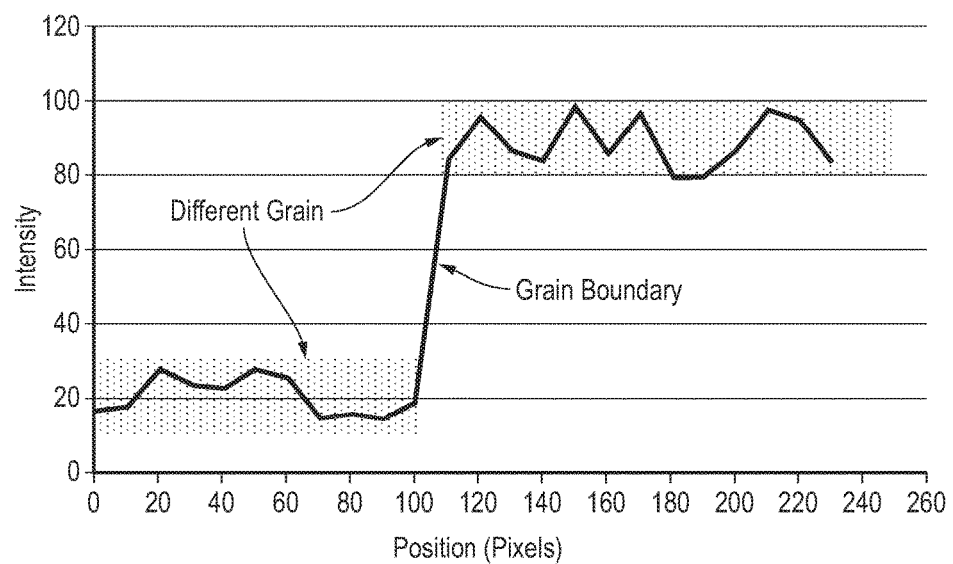
FIG. 4 is a graph showing reflected intensity versus position across a secondary grain boundary.

FIG. 4 shows a (Level 1) graph of absolute intensity as a function of pixel position across a defect boundary. The graph represents the data from a single image.

Therefore, for a full hemisphere of data using all 18 lighting rows and B axis increments of 10 degrees the rig generates 648 photographs each with its associated Level 1 graph.

Figure 5:
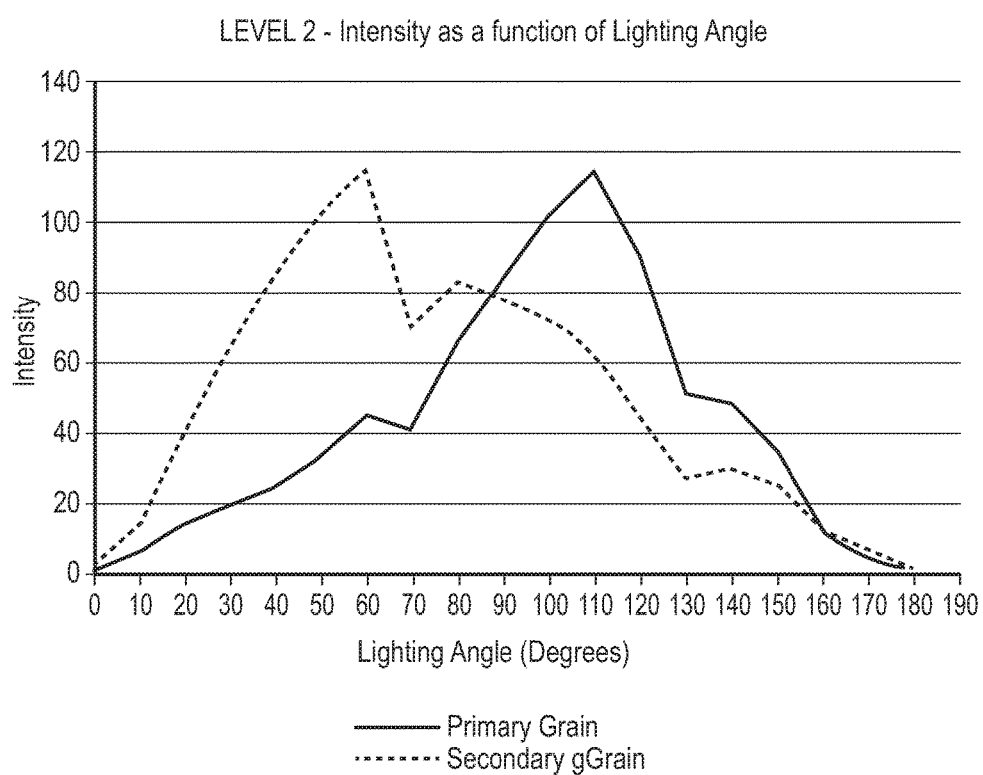
FIG. 5 is a graph showing the reflected intensity from the primary and secondary grains for different lighting angles.

FIG. 5 shows a (Level 2) graph of absolute intensity versus lighting angle showing the primary and secondary grain as separate series. The data from this plot requires a separate analysis of the light reflected from the primary and secondary grains. If the angle between the primary grain and secondary grain is large enough a phase difference between the two peaks can be seen.

Figure 6:
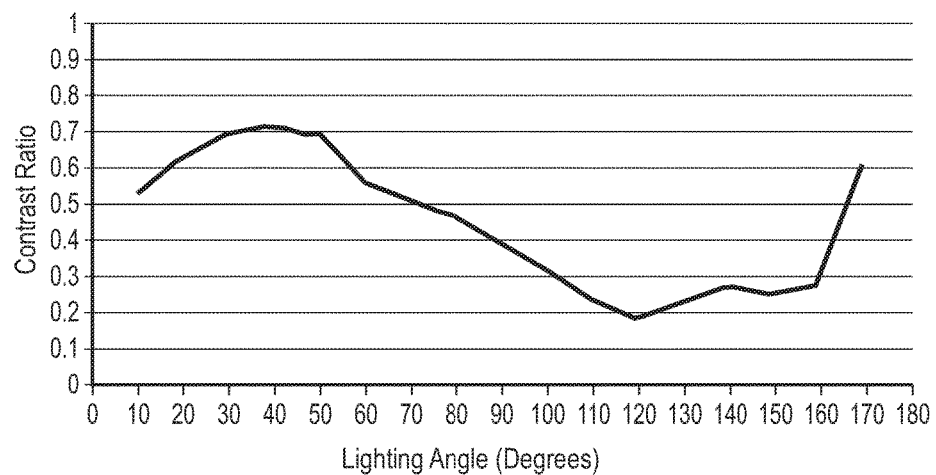
FIG. 6 is a graph showing contrast ratio as a function of lighting angle.

FIG. 6 shows a (Level 3) graph of relative intensity (i.e. the contrast between reflected light returned from the primary grain and the reflected light from the secondary grain) as a function of lighting angle in degrees for a single B axis position (in plane rotation angle). There are a number of methods by which the relative intensity can be calculated, the method used has been found to affect the sensitivity of the system.

There are a number of suitable metrics for expressing the contrast between the primary and secondary grains, as shown below. For example, relative intensity (Equation 1) may be used. As the blade is imaged at multiple rotation angles during the same test run the contrast between the two grains will be inverted at some B axis angles and hence the relative intensity will give both positive and negative values. To avoid this, a contrast ratio (Equation 2) or edge level (Equation 3) calculation may be used.

The basic relative intensity is given by:

$$\frac{I}{I_0} = \frac{I_{Secondary}}{I_{Primary}} \quad \text{Equation 1}$$

The contrast ratio is defined by:

$$CR(\%) = \frac{max - min}{max + min} \quad \text{Equation 2}$$

The edge level is defined by:

$$\Delta I = max - min \quad \text{Equation 3}$$

Equation 2 or 3 can be applied to measure the contrast difference seen in each of the images taken by using the profile in the corresponding Level 1 graph. Repeating this process for every image taken at every lighting position and every B axis angle produces a matrix of contrast values which can then be used to produce the surface plot (Level 4 graph) and the intermediate graph (Level 3).

Figure 7:
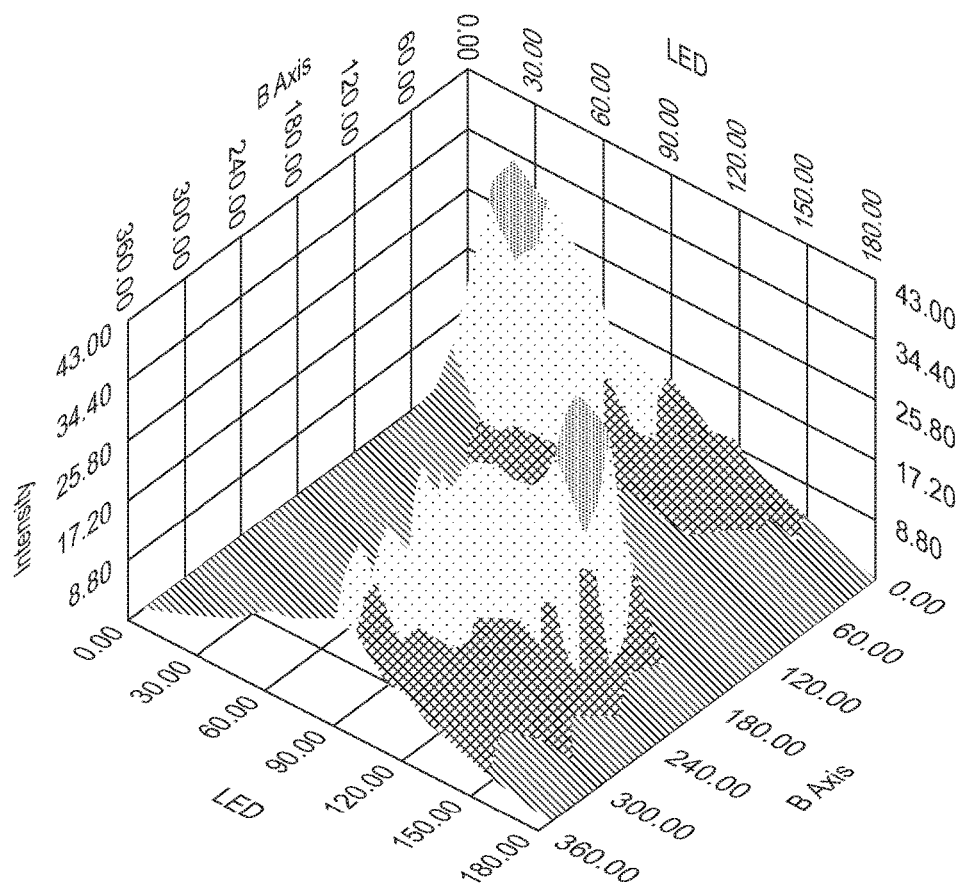
FIG. 7 is a 3D contour plot showing the contrast ratio for different B axis angles and lighting angles.

FIG. 7 shows a (Level 4) graph of contrast as a function of lighting angle and planar rotation/rotary stage position (B axis) resulting in a 3D surface plot. This graph is an amalgamation of the Level 3 graphs taken at different B axis positions. The Level 4 graph is a means of displaying the overall results of a full test on any one particular defect and displaying the contrast over a full hemisphere of different lighting angles.

The Level 1 to 4 graphs may be used to differentiate between different types of defect present in the turbine blades.

Figure 8:
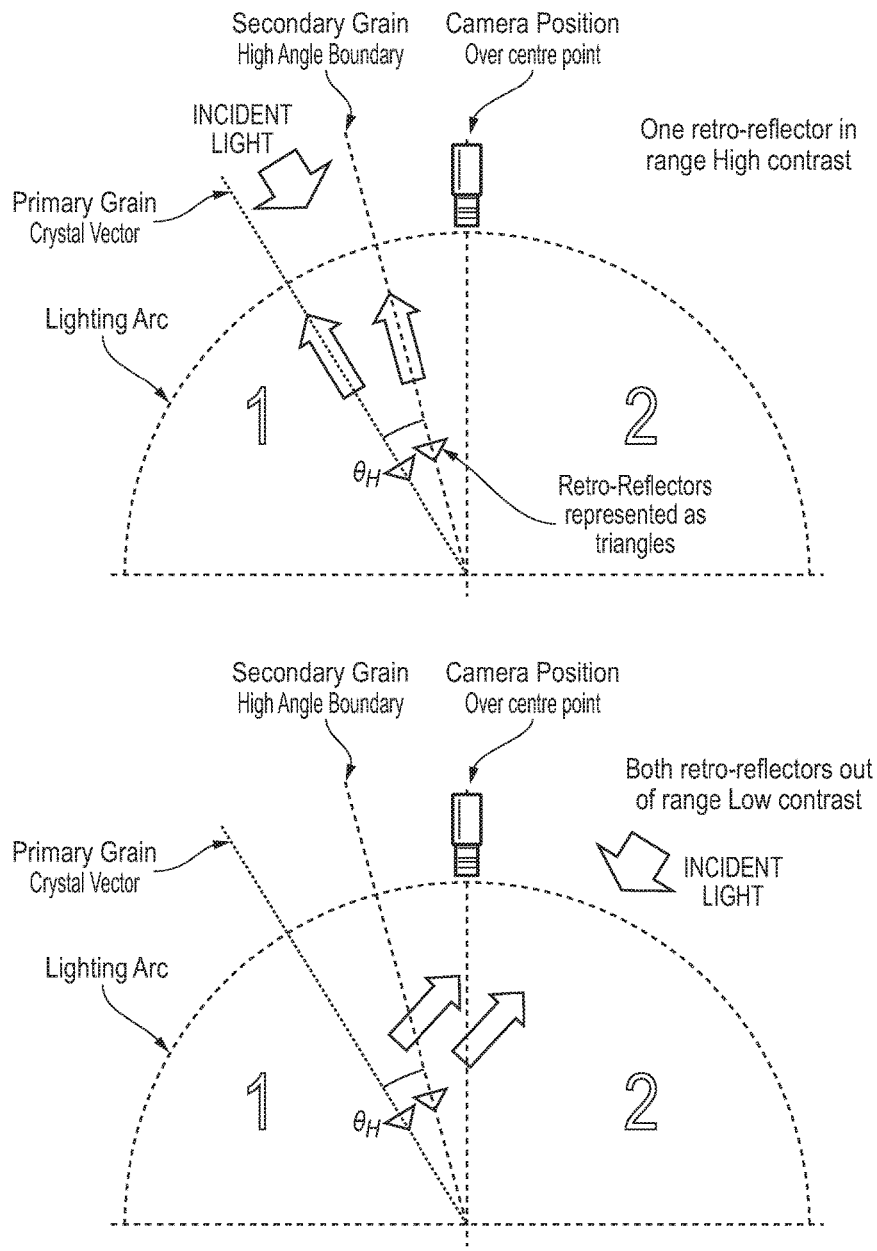
FIG. 8 is a conceptual representation of the reflection of light from a surface having a high angle boundary grain defect at different lighting angles and at a first B axis angle.

FIG. 8 shows the reaction of a secondary grain defect with a high angle boundary ($\theta_H$) to light from different directions, at a B axis angle of 0°. As shown, when illuminated by one of the lighting strips 14 from a first direction (in the first half of the arc, i.e. having an angle less than 90° when measured in a clockwise direction), the retro-reflectors of the primary and secondary grains reflect light in different directions. Accordingly, the intensity of light received at the camera 16 from the primary and secondary grains differs and in this case is greater for the primary grain. At this angle of illumination, the difference in intensity is greatest, such that a high contrast is observed. On the other hand, when illuminated by one of the lighting strips 14 from a second direction (in the second half of the arc, i.e. having an angle greater than 90° when measured in a clockwise direction), the light is out of the angular range of both of the retro-reflectors of the primary and secondary grains such that they reflect very little light. Accordingly, a low contrast is observed at this position.

Figure 9:
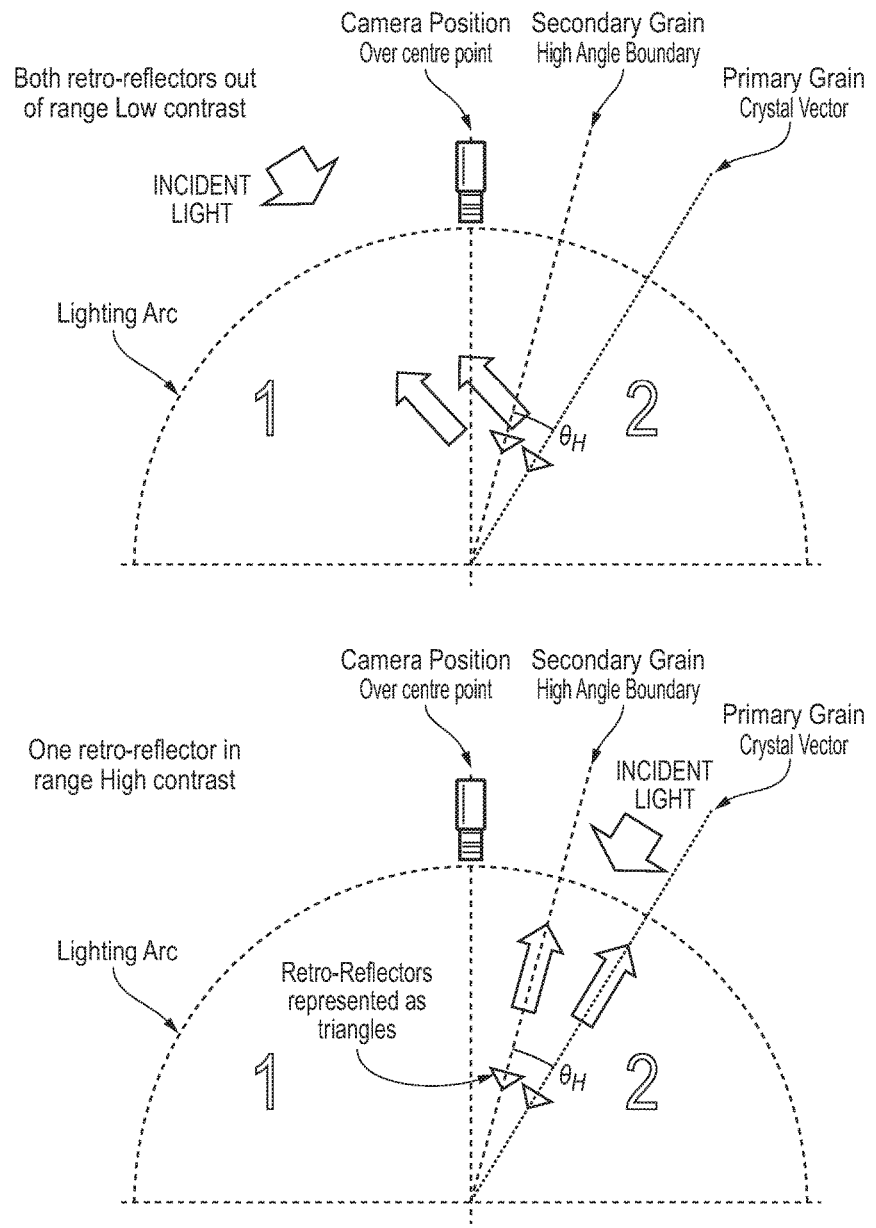
FIG. 9 is a conceptual representation of the reflection of light from the surface having the high angle boundary grain defect at different lighting angles and at a second B axis angle.

FIG. 9 again shows the reaction of the secondary grain defect to light from different directions, but this time at a B axis angle of 180°. As the blade has been rotated through 180°, the primary and secondary grains are now angled in the opposite directions and their positions relative to the centre of the lighting arc 10 are reversed. Consequently, now when illuminated from the first direction, both of the retro-reflectors of the primary and secondary grains are out of range such that they reflect very little light. Accordingly, a low contrast is now observed at this position. On the other hand, when illuminated by one of the lighting strips 14 from the second direction, a greater intensity of light is received from the retro-reflector of the secondary grain compared with that of the primary grain. At this angle of illumination, the difference in intensity is greatest, such that a high contrast is observed.

Figure 10:
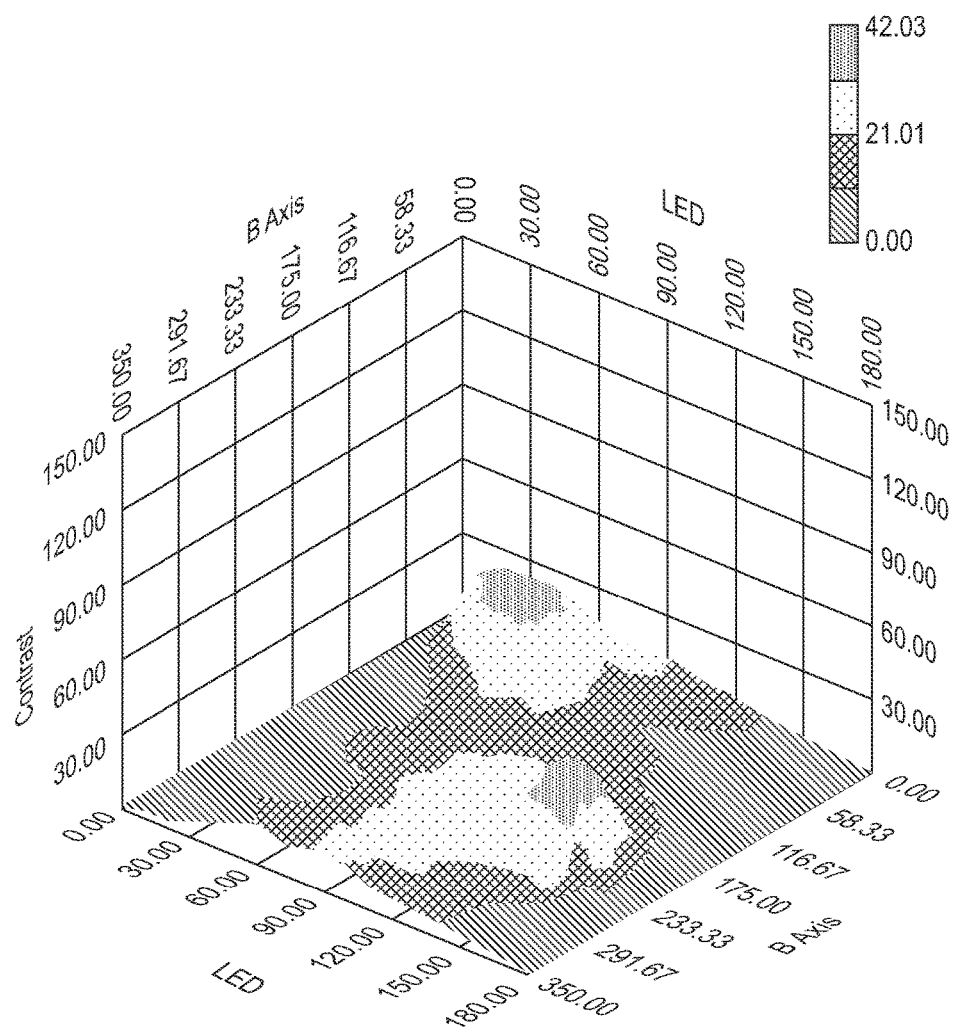
FIG. 10 is a 3D contour plot for the surface shown in FIGS. 8 and 9.

On a contrast ratio graph the high contrast regions of the arc will appear as a peak. If a peak appears at a lighting angle in the first half of the arc when B=0° it will appear at the opposite lighting angle (in the second half of the arc) when the blade is moved through 180°. This is depicted in the 3D surface plot (Level 4) shown in FIG. 10. As shown, at a B axis angle of 0° the contrast between the two grains' peaks is greatest at an illumination angle of around 30°. As the B axis is rotated the peak subsides but then re-emerges again at a lighting angle of around 150°.

A similar contrast ratio graph (although with less prominent peaks) is also observed for low angle boundary secondary grain defects.

Figure 11:
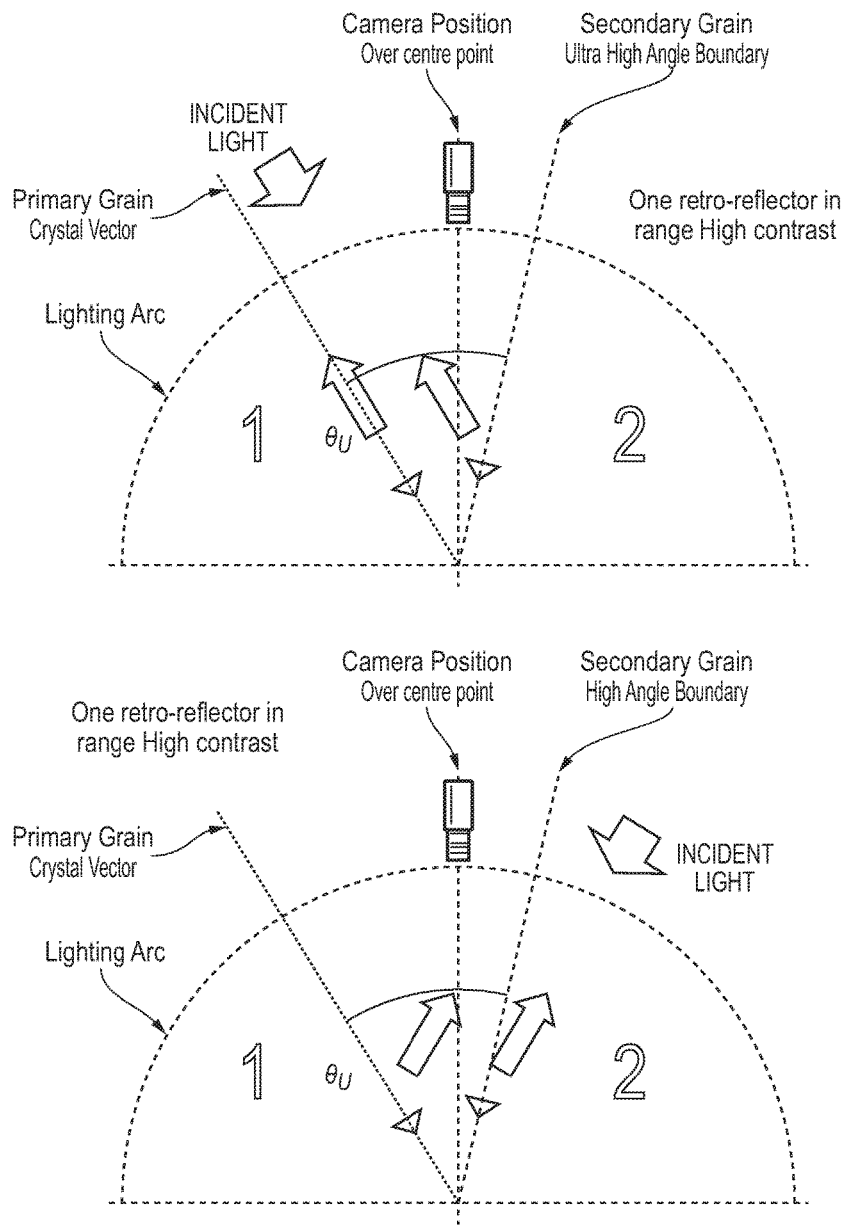
FIG. 11 is a conceptual representation of the reflection of light from a surface having an ultra-high angle boundary grain defect at different lighting angles and at a first B axis angle.
Figure 12:
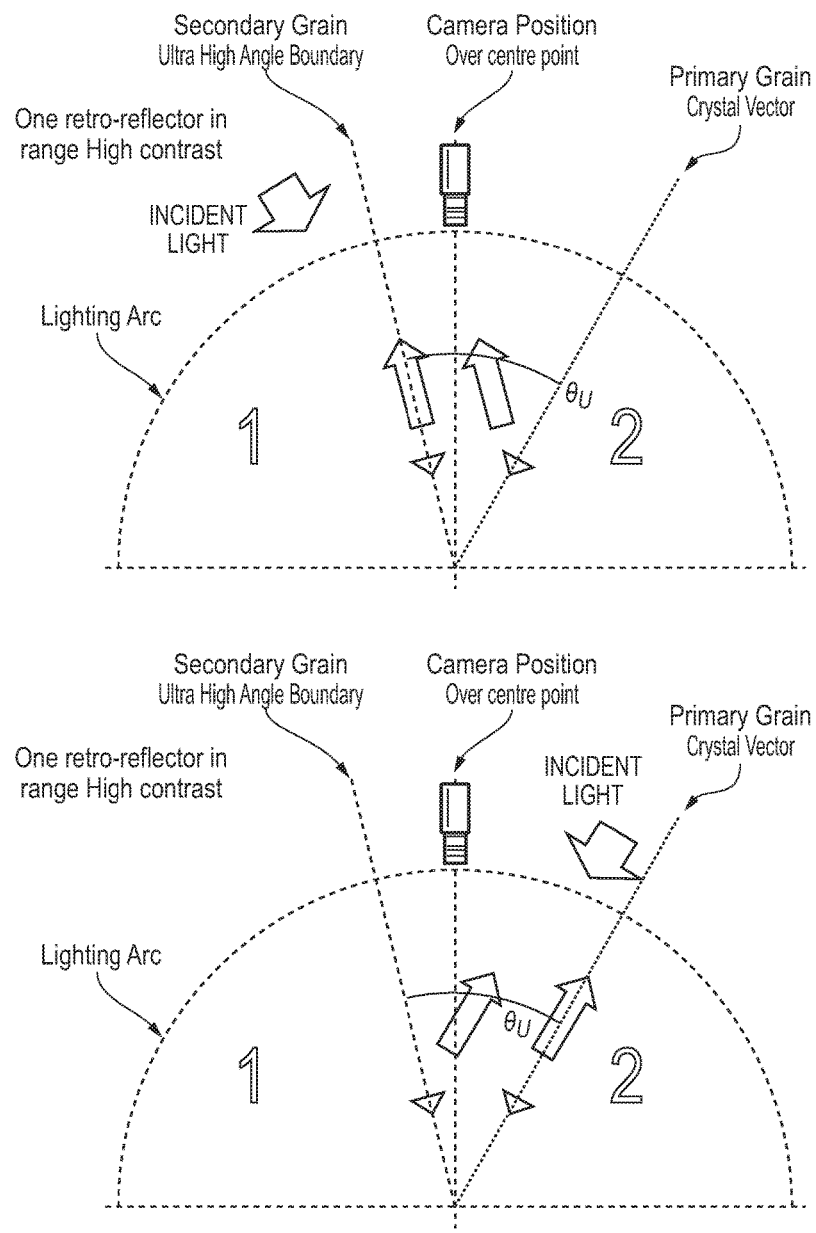
FIG. 12 is a conceptual representation of the reflection of light from the surface having the ultra-high angle boundary grain defect at different lighting angles and at a second B axis angle.

FIGS. 11 and 12 show the reaction of a secondary grain defect with an ultra-high angle boundary ($\theta_U$) to light from different directions, at a B axis angle of 0° and 180° respectively.

Figure 13:
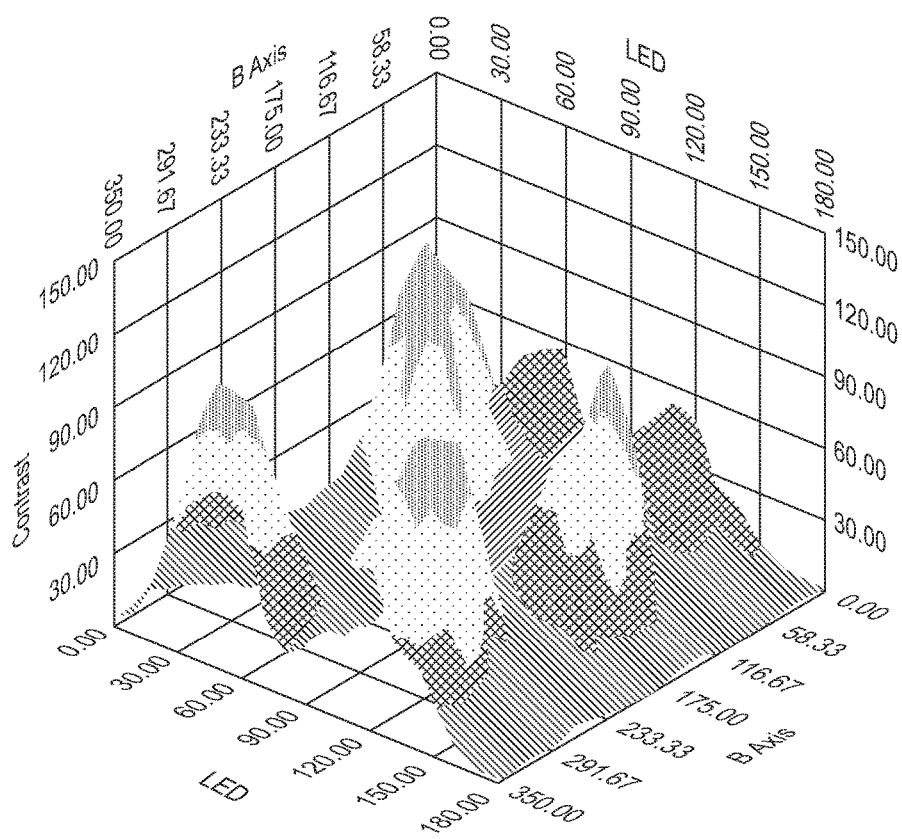
FIG. 13 is a 3D contour plot for the surface shown in FIGS. 11 and 12.

An ultra-high angle boundary may be defined as a defect where the angular offset of the primary and secondary grains is wide enough to straddle the central axis of the arc, as shown. As a result, light projected down onto the turbine blade surface from either side of the lighting arc is within the angular range of either the primary or secondary retro-reflector field, and thus a high contrast region is seen on both sides of the arc. Consequently, the 3D surface plot (Level 4) shown in FIG. 13 displays a total of four peaks. The number of peaks present in the 3D surface plot can therefore be used to differentiate between high and ultra-high angle boundary defects.

The Level 1 to 4 graphs may be also used to differentiate between crystallographic defects and simple scratches or scuffs on the turbine blade.

In contrast to grain defects, scratches and scuffs do not act as retro-reflectors. Instead, scratches and scuffs damage the natural retro-reflector nature of the gamma prime precipitate and leave a "flat" and shiny surface which reflects light as a mirror would.

Figure 14:
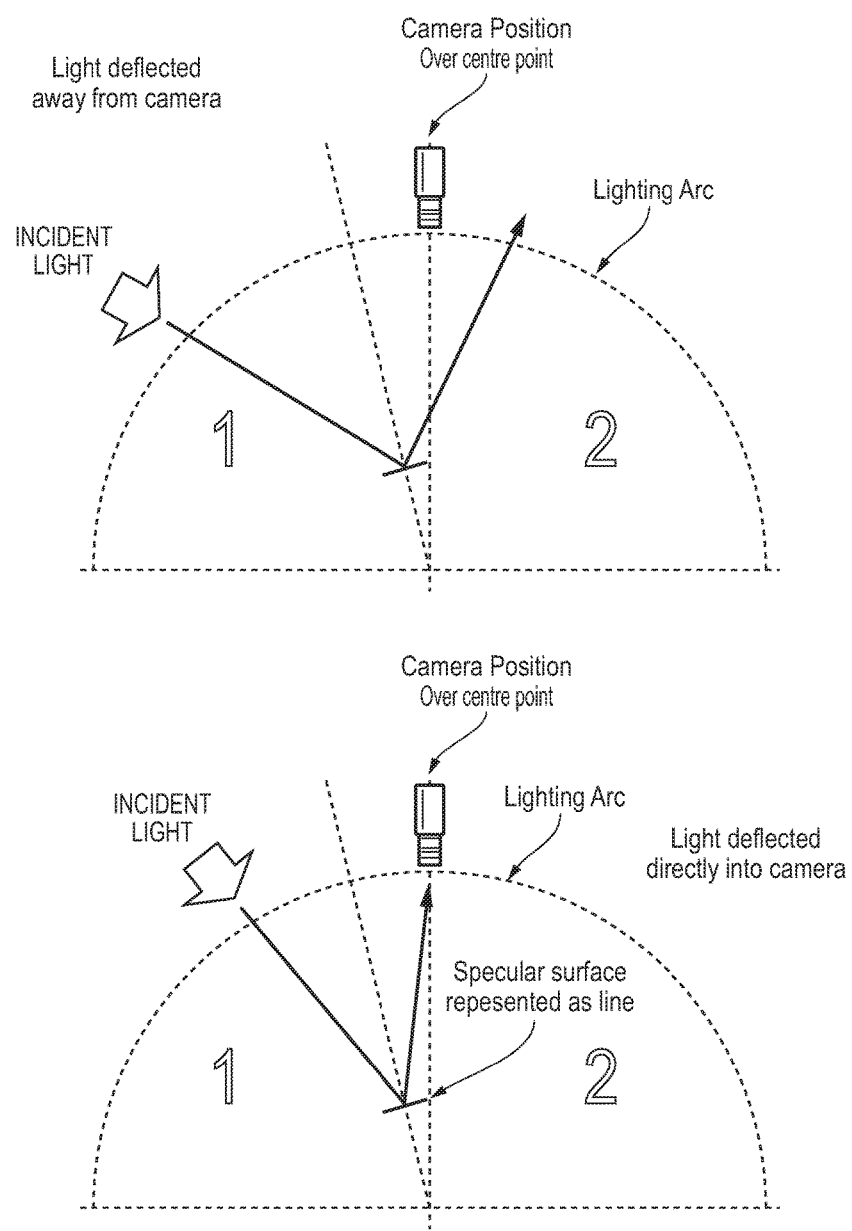
FIG. 14 is a conceptual representation of the reflection of light from a surface having a scratch at different lighting angles.
Figure 15:
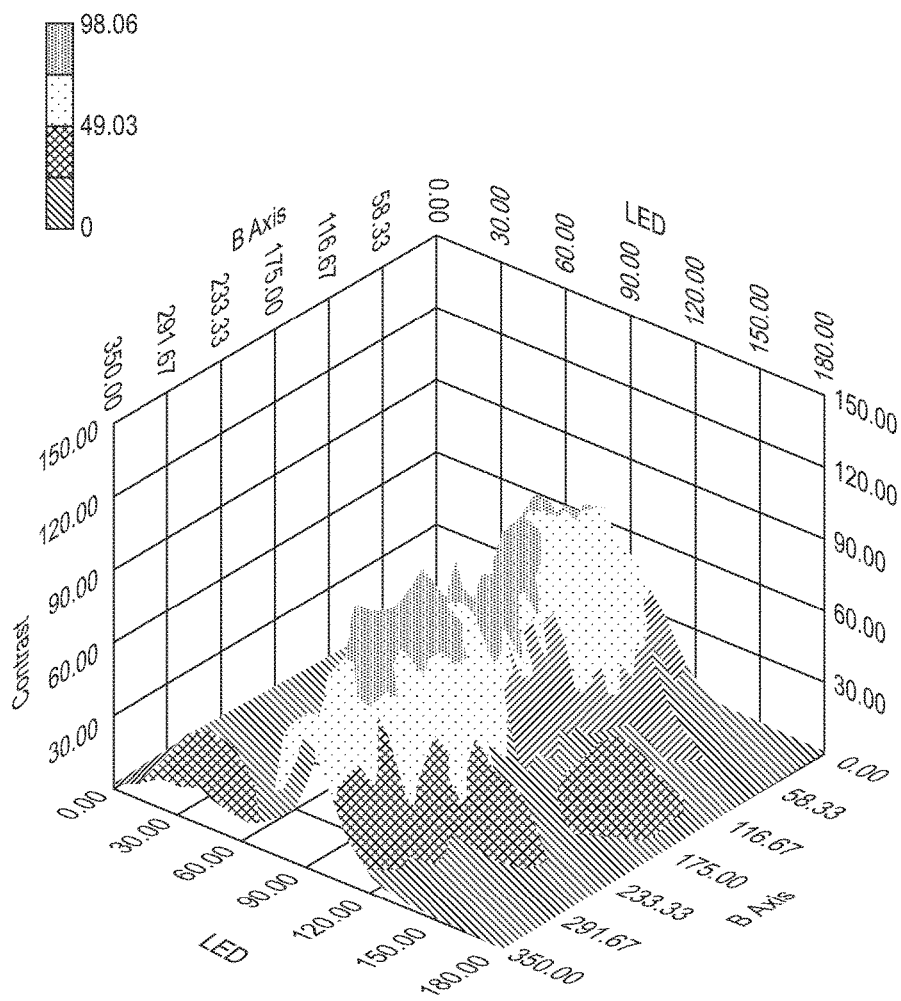
FIG. 15 is a 3D contour plot for the surface shown in FIG. 14.

Consequently, as shown in FIG. 14, light will be reflected away from the camera 16 for the majority of lighting strip positions and there will be only a small number of lighting strip positions which cause the light to be reflected towards the camera 16 so as to produce an intensity peak. Moreover, due to the nature of the scratch and the fact that the surface normal is nominally aligned to the camera 16, the intensity peak occurs close to the zenith of the lighting arc. As a result, when the blade is rotated by 180° the peak will again be close to the zenith and hence a sharp ridge is formed down the centre of the 3D surface plot, as shown in FIG. 15.

The same distinctive shape on the 3D surface plot has been observed for individual narrow scratches and large areas of scratches or scuffed areas. The height of the peak on the 3D surface plot has been found to correlate to the severity of the scratch.

The computer system 6 is configured to execute an analysis algorithm which automatically classifies defects.

The analysis algorithm performs a number of tests on the Levels 1 to 4 graphs, as will be described in detail below. Each of the individual tests returns a verdict of "1" or "0", with "1" supporting evidence for a secondary grain defect and "0" supporting evidence for a scratch or scuff.

Figure 16:
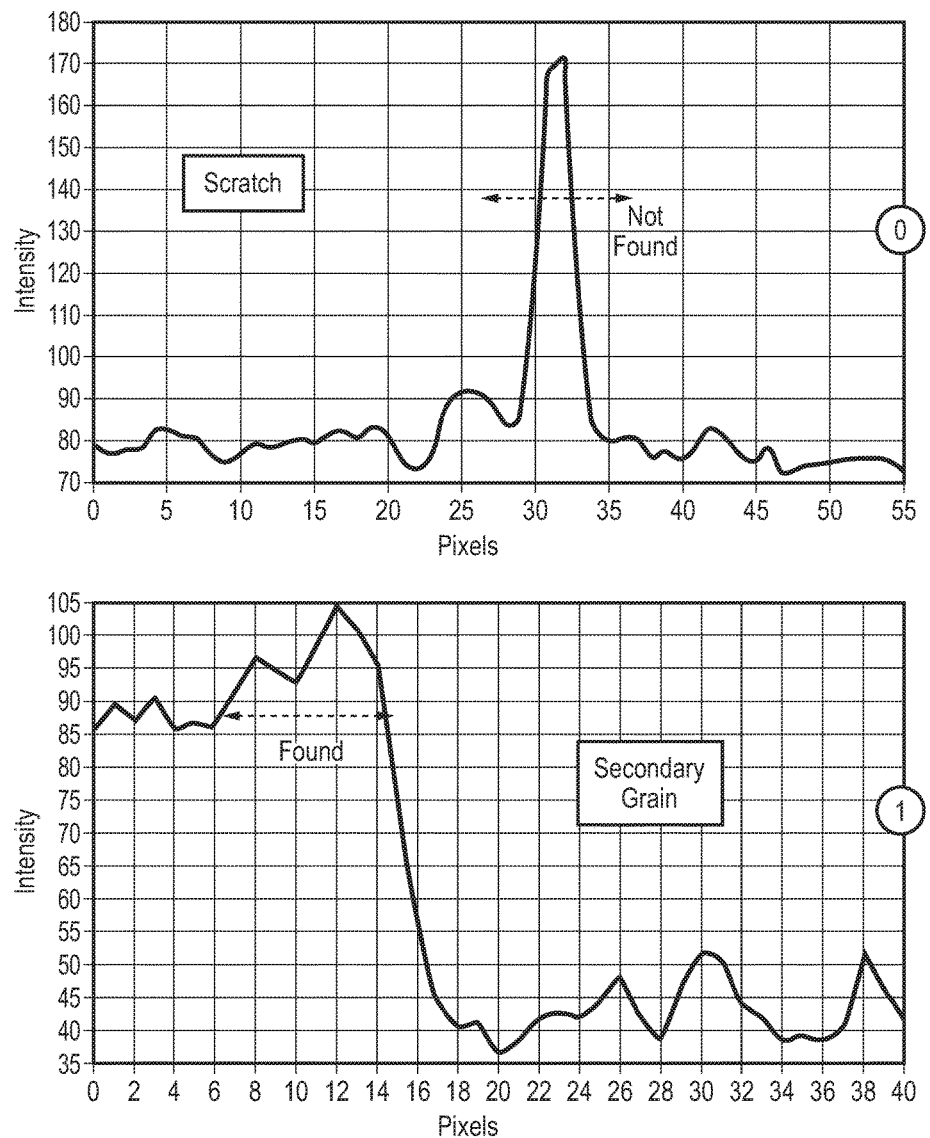
FIG. 16 is an illustration of a first test for distinguishing between secondary grain defects and scratches.

In a first test, the width of the profile in each pixel profile chart (Level 1 graph) is determined. As described above, scratches will typically appear as a peak whereas a crystal defect will be a step. The analysis algorithm determines whether a step is present by checking for a peak wider than 5 pixels at 80% of maximum intensity. If the algorithm finds a step in more than one of the 648 profiles, it will return 1, otherwise it will return 0. This is illustrated in FIG. 16. Here, the scratch shown in the upper plot is not sufficiently wide to be considered a step and so is scored 0, whereas the step in the lower plot is scored 1.

Figure 17A:
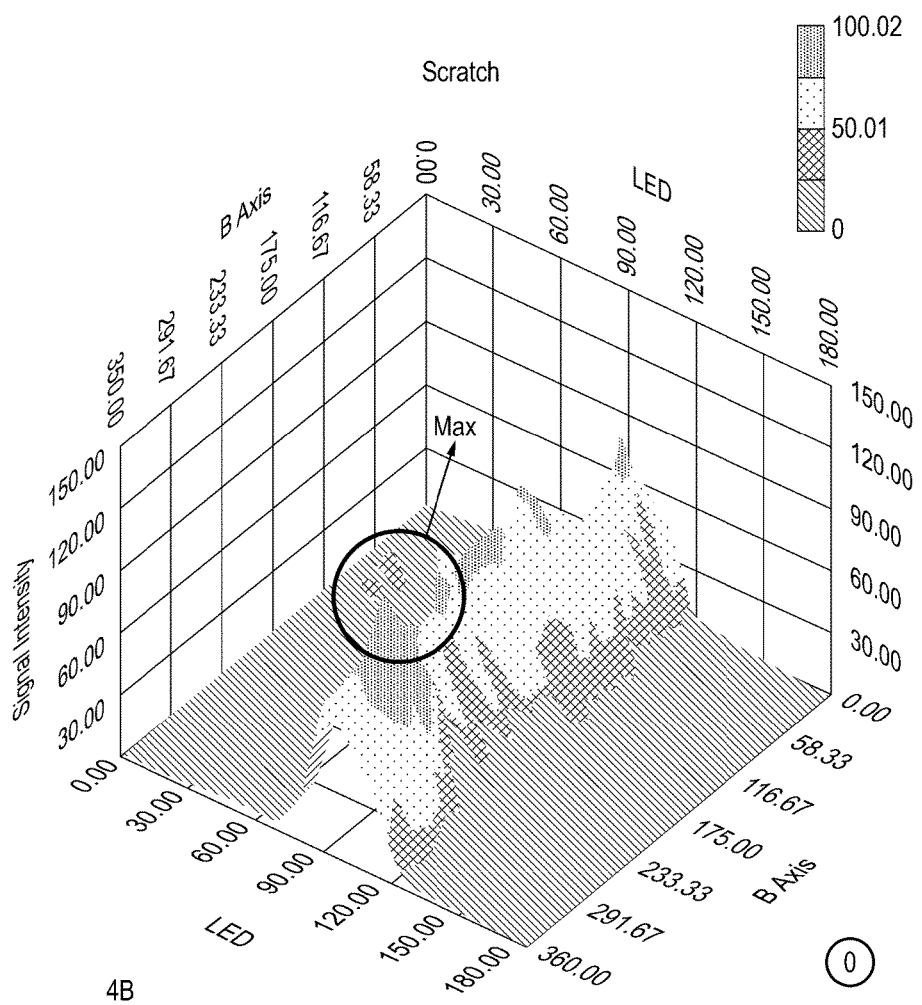
FIG. 17A is an illustration of a second test for distinguishing between secondary grain defects and scratches, and receiving a score of "0."
Figure 17B:
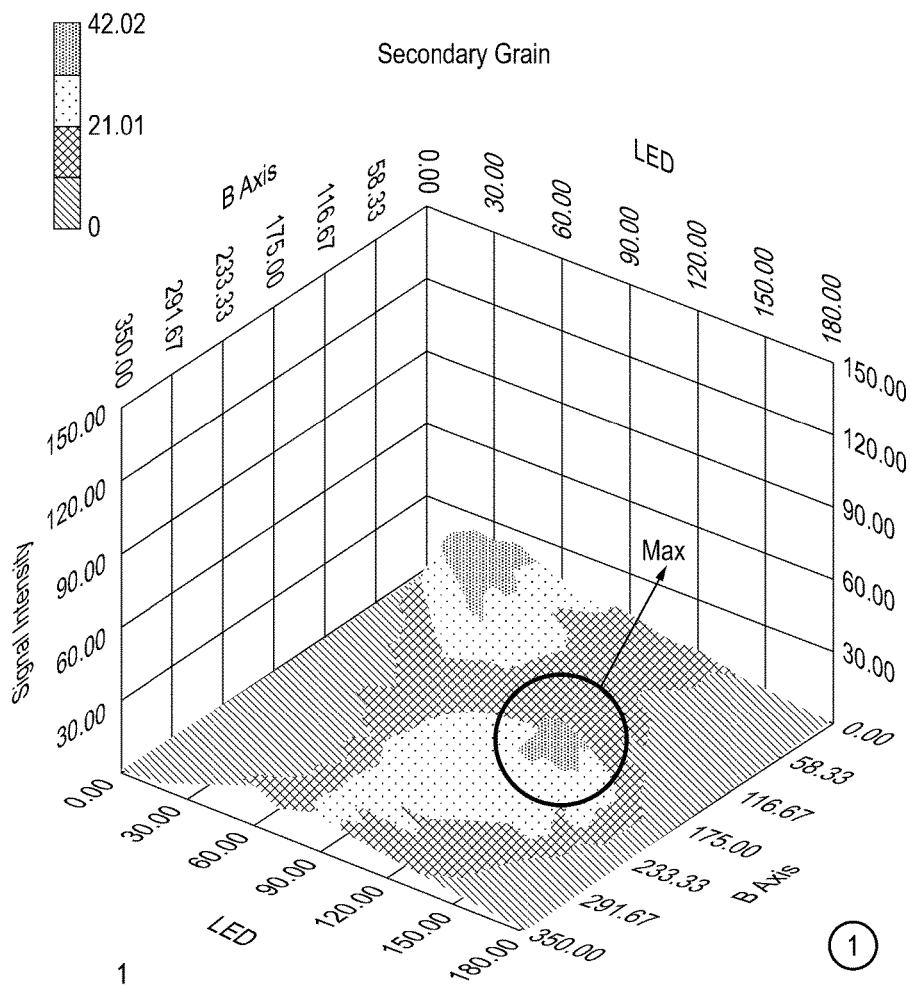
FIG. 17B is an illustration of a second test for distinguishing between secondary grain defects and scratches, and receiving a score of "1."

In a second test, the position(s) of the points of maximum contrast on the 3D surface plot are evaluated. If the maximum contrast lies between the lighting angles of 70° and 110° it is supporting evidence for a scratch; whereas offset, isolated lobes tend to suggest a secondary grain. This is illustrated in FIGS. 17A and 17B. Here, the plot illustrated in FIG. 17A has a maximum contrast at approximately 90° and thus is scored 0, whereas the offset lobes of the plot illustrated in FIG. 17B fall outside of the 70 to 110° window and thus the plot illustrated in FIG. 17B is scored 1.

Figure 18:
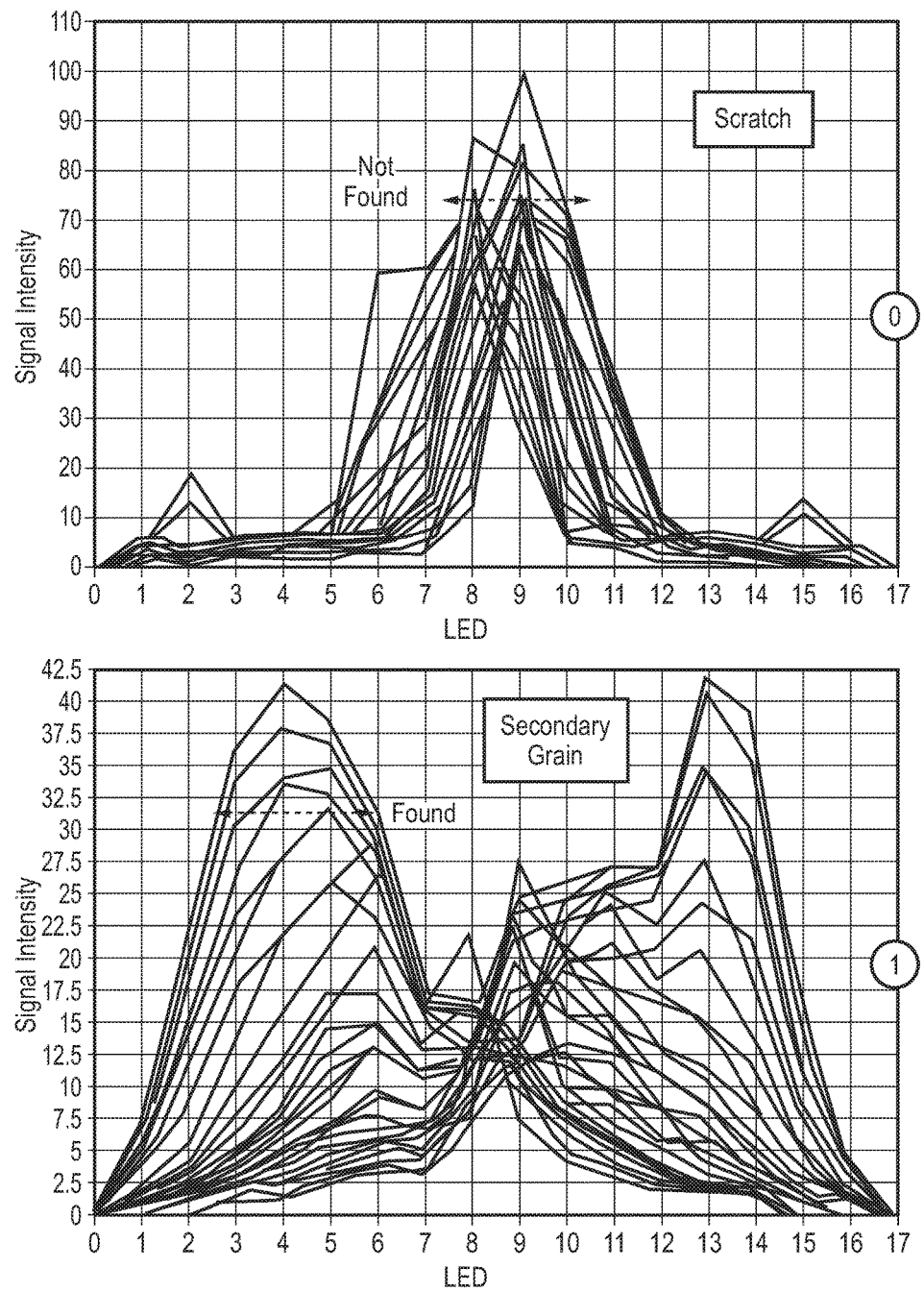
FIG. 18 is an illustration of a third test for distinguishing between secondary grain defects and scratches.

In a third test, the width of the peak(s) themselves are measured. Narrow peaks will be supporting evidence for a scratch whereas wider peaks are more likely to be secondary grains. Although similar in approach to the first test described above, the third test is performed on a contrast versus lighting angle graph rather than an absolute intensity versus pixel position graph. Therefore, similar to the analysis performed in the first test, the algorithm checks the width of each peak for each B axis angle. In other words, if the peak has a width which exceeds a threshold, then it is scored 1, otherwise it is scored 0. This is illustrated in FIG. 18. Here, the upper plot does not have any peaks which exceed the threshold width and thus is scored 0, whereas the lower plot does contain peaks which exceed the threshold width and thus is scored 1. It is noted that the plots shown in FIG. 18 are the 2D equivalent of the Level 4 plots with each B axis angle displayed as a different coloured line. Therefore, it is effectively an end view of the 3D landscape (i.e. viewed from the lighting angle axis). This format could therefore be used as an alternative to the 3D surface plots described previously.

In a fourth test, the continuity of the intensity close to the zenith of the lighting arc (90° as the B axis changes is evaluated. As described previous, scratches exhibit mirror like behaviour such that the contrast intensity tends to remain relatively constant across all B axis angles. In contrast, for a fixed lighting angle, secondary grains display maxima and minima as the B axis rotates. This is illustrated in FIGS. 19A and 19B. Here, the plot illustrated in FIG. 19A exhibits a continuous peak and thus is scored 0, whereas the plot illustrated in FIG. 19B has a discontinuous peak and thus is scored 1. It is noted that the lower plots shown in FIGS. 19A and 19B are the 2D equivalent of the Level 4 plots with each lighting angle displayed as a different coloured line. Therefore, it is effectively a side view of the 3D landscape (i.e. viewed from the B axis angle axis). This format could therefore be used as an alternative to the 3D surface plots described previously.

The lobes of a secondary grain may be symmetrical and close to the zenith of the lighting arc (under certain blade alignment conditions) such that the second test incorrectly yields a 0 rather than a 1. This fourth test is able to distinguish between two aligned lobes and a ridge caused by a scratch.

The algorithm adds the score from each of tests 1 to 4 to provide an overall score which ranges from 0 to 4. The total score can be used to classify the defect. Specifically, total scores of 0 and 1 are classified as scratches, scores of 3 and 4 are classified as secondary grains and a score of 2 is deemed inconclusive. The algorithm is therefore able to distinguish between scratches, which may be deemed cosmetic and thus acceptable, and secondary grains, which are more serious crystal defects and thus may lead to the part being rejected. Blades which return an inconclusive result may undergo further testing using other methods, such as X-ray crystallography. It is anticipated that relatively few results would be inconclusive and so further testing would rarely be required.

The techniques described above have also been found to identify both sliver defects and metal splash defects as secondary grains. Metal splashes occur when molten metal momentarily leaves the surface of the blade during the casting process and reattaches itself. Although metal splash defects are not typically considered to be secondary grains, it is inevitable that the metal splash will have a different crystal structure orientation compared with the remainder of the blade and so may be considered to be a secondary grain defect. The techniques may also be used to identify re-crystallisation defects. These are areas of the blade where the single crystal structure has failed and the material has cooled into its natural polycrystalline state. Polycrystalline defects may be considered as multiple secondary grains next to one another over a confined area of the surface. If a sample section line is drawn from the primary grain structure into the first of the secondary crystals only (i.e. not including the other crystals) the results returned are the same as for a secondary grain. Extending the sample area to include multiple crystal boundaries would produce a series of edges on the Level 1 profile plots and multiple lobes on the Level 4 surface plot.

It will be appreciated that the analysis algorithm may score the tests differently from the scheme described above. For example, the tests may be weighted differently so that more conclusive tests contribute more to the final score. The results of each test need also not be binary (i.e. 0 or 1), but may instead use decimal numerals to form a sliding scale (e.g. from 0 to 10). The score may be calculated based on bands, rather than a simple threshold as described previously.

It may not be necessary to use each of the graphs (Levels 1 to 4) or tests (1 to 4) described previously to provide a satisfactory determination regarding the nature of the defect. In particular, the Level 1 plot and the first test may be omitted. Further, it will be appreciated that the tests may be completed based on the raw data for the relevant plots, but that the plots themselves need not be defined nor output for inspection by a user. Accordingly, the computer system 6 may only output the ultimate determination of the results of the tests (i.e. scratch, secondary grain or inconclusive) and/or the individual test results.

Instead of measuring the intensity along a line intersecting the secondary grain boundary, a box (which may be square or any other shape) could instead be drawn around the region which contains the defected region and the non-defected region. The defined area of the image can then be plotted as a histogram showing the greyscale intensity as a function of pixel count. This is shown in FIG. 20. Instead of containing a step, this alternative graph contains two peaks. The distance $\Delta I$ between the two peaks is equivalent to measuring the step height, but may provide more accurate results as it is more immune to system noise, localised variation in intensity, as well as allowing the system to be more robust. This method can then be repeated for every lighting angle, using the $\Delta I$ values as before to build up a 3D surface plot. As a further alternative, a histogram (or simply the average intensity) of a box located entirely within the defected region and a histogram (or simply the average intensity) of a box located entirely within the non-defected region may be used to determine the difference in intensity $\Delta I$. In a similar manner, the intensity of a single point within the defected region and a single point within the non-defected region may be used.

Although the analysis algorithm has been described with reference to the outputs generated by the imaging rig 4, it will be appreciated that other apparatus may be used. For example, a hemispherical lighting apparatus may be used to avoid having to rotate the component being tested, as described in EP 2846156. Each B axis angle and lighting angle may be considered to correspond to the polar angle $\theta$ and azimuthal angle $\varphi$ used in a spherical coordinate system (the radius r is not significant for determining the direction of light relative to the component being tested; akin to longitude and latitude measurements). For a hemispherical lighting apparatus, the polar angle $\theta$ and azimuthal angle $\varphi$ may be used to identify the light source and its direction. Further, a light detector may be used instead of a camera, if desired, provided it has sufficient resolution to capture the required data.

The apparatus and methods described above are not limited to the testing of turbine blades and may be applied to other components which are intended to have a single crystal structure.

The computer system 6 may be a standard personal computer configured via software and/or hardware to control the imaging rig 4 and to execute the analysis algorithm. Alternatively, the computer system 6 may be a standalone device for this purpose.

The method offers a number of commercial advantages in the manufacture of components with intended monocrystalline structures. For example, where the defect is classified as a secondary grain it is possible to make a decision to stop any further manufacturing treatments on the component unless the difference in grain angle is below a threshold. Where the defect is classified as a scratch it is possible to decide whether to stop any further manufacturing treatments on the component or to ignore the scratch or to decide to repair the scratch.

The invention is not limited to the embodiments described herein, and may be modified or adapted without departing from the scope of the present invention.

The invention claimed is:

1. A method of classifying whether a defect in a component having a monocrystalline structure with a primary grain is a scratch or a secondary grain, the method comprising:
    illuminating a surface of the component containing the defect with a beam of light from a plurality of different spherical directions centred on the surface of the component containing the defect;
    for each illumination direction, measuring an intensity of light reflected by the surface of the component containing the defect and received by a detector;
    determining a contrast value between a region with higher intensity and a region with lower intensity for each illumination direction;
    analysing the contrast values by performing a plurality of tests selected from the following:
        (a) determining whether the region with higher intensity exceeds a predetermined width;
        (b) identifying the illumination direction which produces a maximum contrast value, and determining whether the illumination direction falls outside of a predetermined region centred on the detector;
        (c) identifying a peak in the contrast values, and determining whether a width of the peak exceeds a predetermined threshold and the peak extends over a range of illumination directions; and
        (d) determining whether the contrast values contain a plurality of discontinuous peaks; and
    determining whether the defect is a scratch or a secondary grain based on an outcome of each of the plurality of tests.

2. The method as claimed in claim 1, wherein the outcome of each of the plurality of tests is allocated a score and a total score determines whether the defect is a scratch or a secondary grain.

3. The method as claimed in claim 1, wherein the defect is determined as a secondary grain if the outcome of more than half of the plurality of tests are positive.

4. The method as claimed in claim 1, wherein the defect is determined as a scratch if the outcome of less than half of the plurality of tests are positive.

5. The method as claimed in claim 1, further comprising, when the defect is determined as a secondary grain, determining the number of peaks defined by the contrast values; and
when there are four peaks, identifying the defect as an ultra-high angle grain defect.

6. The method as claimed in claim 1, further comprising, when the defect is determined as a scratch, determining a severity of the scratch based on a height of the peak in the contrast values.

7. The method as claimed in claim 1, wherein the surface is illuminated by a plurality of light sources arranged in an arc and the component is rotated relative to the plurality of light sources by set increments to define the spherical directions.

8. The method as claimed in claim 7, wherein each of the illumination directions is defined by a lighting angle of the light source on the arc and a rotation angle of the component to the light source.

9. The method as claimed in claim 8, wherein test (c) determines whether the peak extends over a range of lighting angles which exceeds a predetermined threshold and/or wherein test (d) determines whether the peaks are discontinuous across a plurality of rotation angles of the component to the light source.

10. The method as claimed in claim 1, wherein the contrast value is determined by measuring the intensity of light along a line intersecting the defect.

11. The method as claimed in claim 1, wherein the contrast value is determined by measuring an intensity of each pixel within an area containing the defect and plotting the intensity of each of the pixels on a histogram.

12. The method as claimed in claim 1, wherein the contrast value is determined by measuring the intensity of light reflected by the defect and the intensity of light reflected by a non-defected region.

13. The method as claimed in claim 12, wherein the intensity of light reflected by the defect is measured for each pixel of a box located entirely within the defect and the intensity of light reflected by the non-defected region is measured for each pixel of a box located entirely within the non-defected region.

14. The method as claimed in claim 13, wherein the intensity of the pixels is plotted on a histogram for the defect and a histogram for the non-defected region.

15. The method as claimed in claim 1, further comprising the step of determining one or more future processes to be performed on the component based on the outcome of each of the plurality of tests.

16. The method according to claim 15, wherein one of the future processes is machining out the scratch.

17. A method of classifying whether a defect in a turbine blade having a monocrystalline structure with a primary grain is a scratch or a secondary grain, the method comprising:
illuminating a surface of the turbine blade containing the defect with a beam of light from a plurality of different spherical directions centred on the surface of the turbine blade containing the defect;
for each illumination direction, measuring an intensity of light reflected by the surface of the turbine blade containing the defect and received by a detector;
determining a contrast value between a region with higher intensity and a region with lower intensity for each illumination direction;
analysing the contrast values by performing a plurality of tests selected from the following:
(a) determining whether the region with higher intensity exceeds a predetermined width;
(b) identifying the illumination direction which produces a maximum contrast value, and determining whether the illumination direction falls outside of a predetermined region centred on the detector;
(c) identifying a peak in the contrast values, and determining whether a width of the peak exceeds a predetermined threshold and the peak extends over a range of illumination directions; and
(d) determining whether the contrast values contain a plurality of discontinuous peaks; and
determining whether the defect is a scratch or a secondary grain based on the outcome of the plurality of tests.

* * * * *